(12) United States Patent
Merali

(10) Patent No.: US 7,267,937 B2
(45) Date of Patent: Sep. 11, 2007

(54) **FACILE DIAGNOSIS AND MONITORING OF *PNEUMOCYSTIS CARINII* INFECTION**

(75) Inventor: Salim Merali, Queens, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/477,980

(22) PCT Filed: May 20, 2002

(86) PCT No.: PCT/US02/15622

§ 371 (c)(1),
(2), (4) Date: Aug. 19, 2004

(87) PCT Pub. No.: WO02/094083

PCT Pub. Date: Nov. 28, 2002

(65) Prior Publication Data

US 2005/0032035 A1    Feb. 10, 2005

Related U.S. Application Data

(60) Provisional application No. 60/292,084, filed on May 18, 2001.

(51) Int. Cl.
*C12Q 1/00* (2006.01)
*C12Q 1/02* (2006.01)
(52) U.S. Cl. .............................. 435/4; 435/29; 435/34
(58) Field of Classification Search ................ 435/4, 435/29, 34
See application file for complete search history.

(56) References Cited

U.S. PATENT DOCUMENTS 6,020,139 A * 2/2000 Schwartz et al. ............ 435/7.1

OTHER PUBLICATIONS

Merali et al. (Journal of Biological Chemistry, 2000, vol. 275 No. 20, pp. 14958-14963).*

* cited by examiner

*Primary Examiner*—Robert A. Zeman
(74) *Attorney, Agent, or Firm*—Klauber & Jackson

(57) ABSTRACT

Significantly low circulating S-adenosylmethionine levels were found to be diagnostic for human *Pneumocystis carinii* infection, and rise in levels towards normal correlated with successful treatment. Diagnosis of *P. carinii* injection and monitoring of progress of treatment based thereon are described.

3 Claims, 3 Drawing Sheets

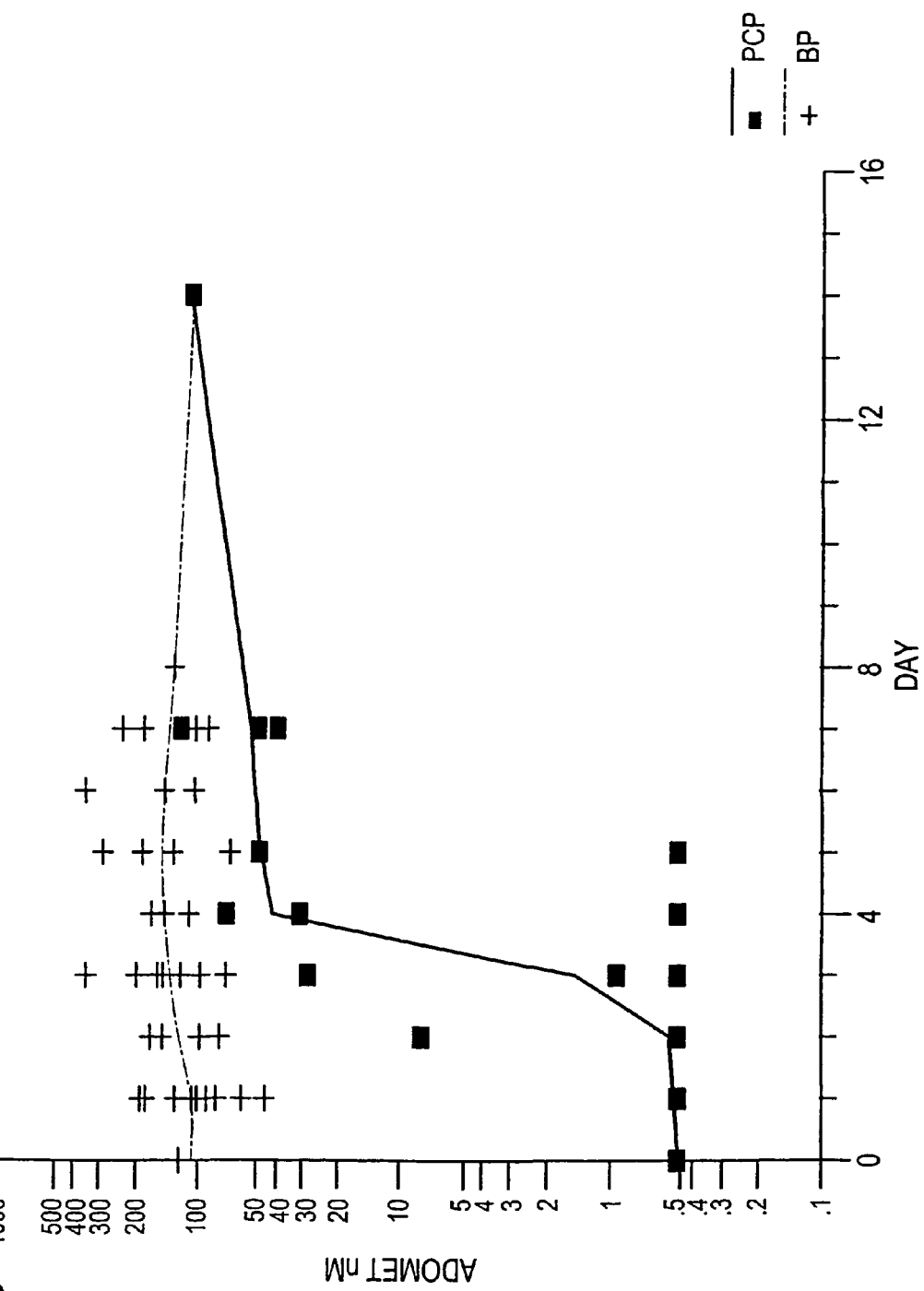

FACILE DIAGNOSIS AND MONITORING OF *PNEUMOCYSTIS CARINII* INFECTION

RELATED APPLICATIONS

The present application is a National Stage Application claiming the priority of copending PCT/U502/15622, filed on May 20, 2002, which claims priority to U. S. Provisional Application Ser. No. 60/292,084, filed on May 18, 2001, the disclosures of both of which are incorporated by reference herein in their entireties. Applicants claim the benefit of this application under the applicable provisions of 35 U.S.C. §119 and 35 U.S.C. §120.

GOVERNMENTAL SUPPORT

The research leading to the present invention was supported in part by the United States Public Health Service Grants RO1 A141947. The government may have certain rights in the present invention.

BACKGROUND OF THE INVENTION

*Pneumocystis carinii* is a fungus that causes *P. carinii* pneumonia (PCP) in people with AIDS, patients undergoing cancer chemotherapy, and others with conditions causing severe immunosuppression. Although the frequency of PCP in HIV-infected persons has decreased dramatically over the fast 8 years, due first to widespread prophylaxis against PCP and more recently to the reduced immunosuppression brought on by improved anti-HIV therapy, PCP remains common in AIDS patients. A large portion of all HIV infections are in Africa yet PCP there was considered rare. However, a recent South African survey reports that PCP is the most common opportunistic infection associated with AIDS in that country—for persons of African as well as European origin (Mahomed et al., 1999, *East Afr Med J.* 76:80-4). An entirely new risk for PCP was identified by a study of autopsy specimens in the UK and Chile. After eliminating all cases of HIV infection, analysis of the data suggested that PCP plays a role in a significant number of cases of sudden infant death syndrome (Vargas et al., 1999, *Clin Infect Dis.* 29:1489-93).

Treatment for PCP is less than ideal with frequent severe side effects from the two most effective drugs, pentamidine and the combination of trimethoprim and sulfamethoxazole (cotrimoxazole, TMP-SMZ) (Wilkin, A., and Feinberg, J. (1999) *Am. Fam. Physician* 60, 1699-1708, 1713-1714). The mortality rate also remains high (21.5%) (Azoulay, E., Parrot, A., Flahault, A., Cesari, D., Lecomte, I., Roux, P., Saidi, F., Fartoukh, M., Bernaudin, J. F., Cadranel. J., and Mayaud, C. (1999) *Am. J. Respir. Crit. Care Med.* 160, 493-499).

Diagnostic methods for PCP are less than ideal. Although bronchoscopy with bronchioalveolar lavage is 95% sensitive, it is expensive, invasive and requires skilled personnel. Induced sputum, an alternative method of diagnosis, is noninvasive but is often much less sensitive (80%). Moreover, the ability to assess treatment effectiveness by means other than clinical improvement is lacking other than by the aforementioned diagnostic methods.

S-Adenosyl-L-methionine (interchangeably referred to herein as S-adenosylmethionine, AdoMet, or SAM) plays a pivotal role in the physiology of all cells, both as methyl donor in myriad of biological and biochemical events and as a precursor of polyamines. About 95% of AdoMet is used for transmethylation reactions in which the N-methyl group of the methionine moiety is transferred to large molecules such as proteins, complex lipids, and DNA or to small molecules to form lecithin, regenerate methionine, etc. (Cohen, S. (1998) *A Guide to Polyamines*, Oxford University Press, Oxford). The remaining 2-5% of AdoMet is decarboxylated to become the aminopropyl donor for synthesis of the essential polyamines spermidine and spermine (Newman, E. B., Budman, L. I., Chan, E. C., Greene, R. C., Lin. R. T., Woldringh, C. L., and D'Ari, R. (1998) *J. Bacteriol.* 180, 3614-3619). Transmethylation reactions result in the formation of S-adenosylhomocysteine which is then hydrolyzed by S-adenosylhomocysteine hydrolase to form adenosine and homocysteine. Decarboxylation of AdoMet is catalyzed by S-adenosylmethionine decarboxylase producing decarboxylated AdoMet, an intermediate committed to polyamine biosynthesis. Decarboxylated AdoMet donates an aminopropyl group to putrescine to form spermidine or to spermidine to form spermine. The end product of the aminopropyl transfer reactions is methylthioadenosine which is cleaved by a specific phosphorylase, the products being recycled in various ways to methionine and purines, respectively. A comprehensive review of polyamine metabolism and function has been published (Cohen, ibid.).

It is towards a facile means for both diagnosing *P. carinii* infection in humans and monitoring the effectiveness of treatment of the infection that the present invention is directed.

The citation of any reference herein should not be deemed as an admission that such reference is available as prior art to the instant invention.

SUMMARY OF THE INVENTION

The present invention is generally directed to the diagnosis and to the monitoring of the progress of infection and treatment of *Pneumocystis carinii* in a human by measuring the level of S-adenosylmethionine (AdoMet) in the blood, and basing the diagnosis on a standard level of uninfected individuals, or for monitoring changes over time on the individual's previous values. Infection of humans by *P. carinii* is associated with a significantly decreased level of S-adenosylmethionine in circulation; successful treatment of human *P. carinii* infection results in an increase and normalization in such levels.

In one embodiment, a method for identifying the presence of a *Pneumocystis carinii* infection in a human is provided by carrying out at least the steps of a) obtaining a blood sample from the human; b) measuring the level of S-adenosylmethionine in the blood sample; and c) correlating a S-adenosylmethionine level below that of an uninfected standard level as indicating the presence of a *Pneumocystis carinii* infection in the human. By way of non-limiting example, the human may be infected with HIV, have AIDS, have cancer, may be immunosuppressed, or may be otherwise susceptible to infection by *Pneumocystis carinii*. In a preferred embodiment, the blood sample is a plasma sample or a serum sample; most preferred is plasma.

In another embodiment of the invention, a method for monitoring changes over time in the level of infection of *Pneumocystis carinii* in a human is provided by carrying out at least the steps of a) obtaining a series of sequential blood samples over time from the human; b) measuring the level of S-adenosylmethionine in the blood samples; and c) correlating an increase, decrease or no change in the level of S-adenosylmethionine in the blood samples over time with a decrease, increase, or no change, respectively, in the level of infection of *Pneumocystis carinii* infection in the human. At least two samples are necessary for monitoring changes in levels over time, but many samples may be taken and evaluated over the course of treatment and afterwards. In a non-limiting example, the human may be infected with HIV, may have AIDS, may have cancer, may be immunosuppressed, or may be otherwise susceptible to infection by *Pneumocystis carinii*. In a preferred embodiment, the blood samples are plasma or serum; most preferably it is plasma. The human may be undergoing treatment for the *Pneumocystis carinii* infection.

These and other aspects of the present invention will be better appreciated by reference to the following drawings and Detailed Description.

BRIEF DESCRIPTION OF THE DRAWINGS

FIG. 3 shows the chances over time in patients with PCP being treated, compared to a group of patients with bacterial pneumonia being treated.

DETAILED DESCRIPTION OF THE INVENTION

Figure 1:
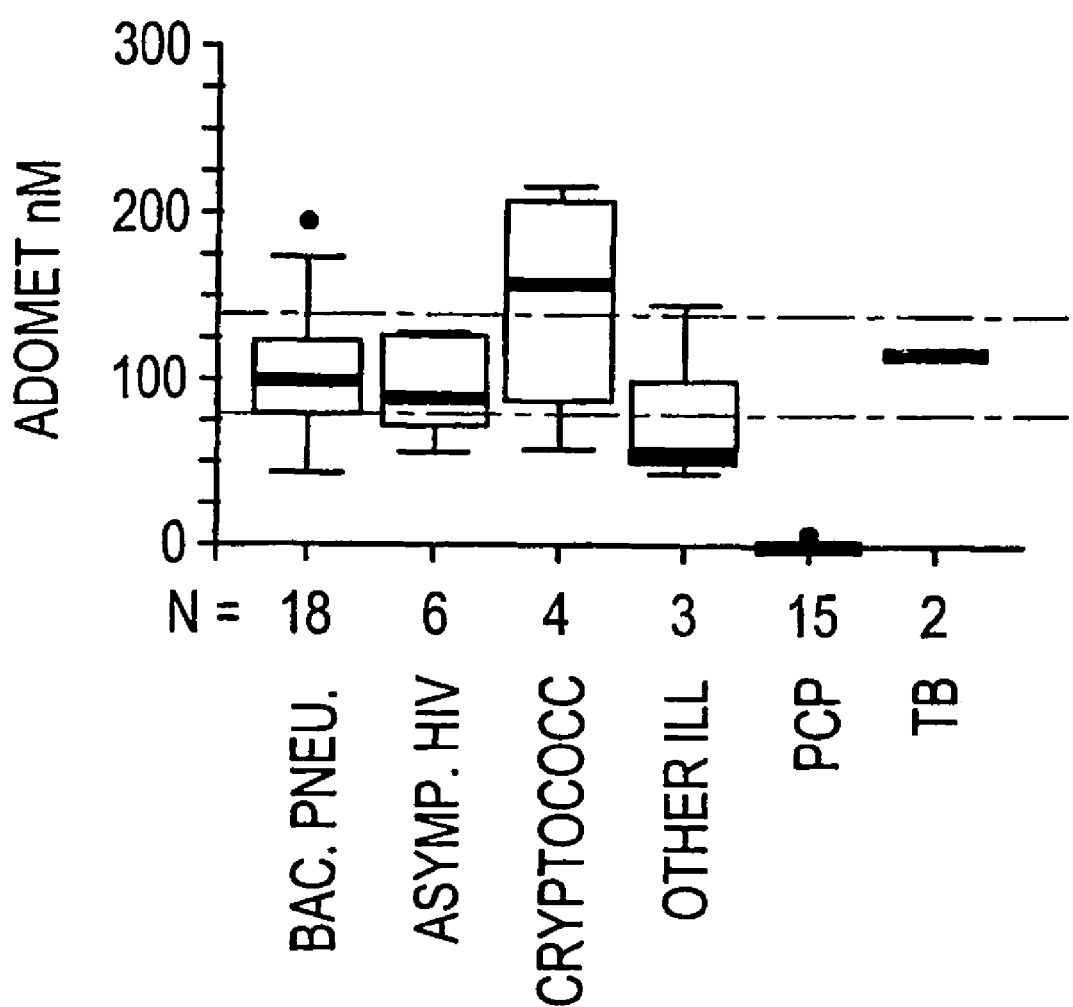
FIG. 1 shows the initial plasma S-adenosylmethionine levels in HIV+ patients with PCP, bacterial pneumonia, cryptococcosis, tuberculosis, miscellaneous conditions, and HIV+ patients without another diagnosis.

The present inventor has discovered the utility of measuring circulating S-adenosylmethionine levels in human patients for the diagnosis of *P. carinii* infection, and its further utility for the monitoring of infection during treatment for the infection. As will be seen in the Examples below, humans infected with *P. carinii*, particularly HIV-infected patients, have a significantly decreased level of S-adenosylmethionine compared with otherwise-healthy HIV patients who are not infected with *P. carinii*, and also have significantly decreased levels compared to HIV patients infected with other organisms, including tuberculosis, cryptococcosis, and those with bacterial pneumonia. When all HIV patients without *P. carinii* infection are compared to those with *P. carinii* infection, the differences are dramatic and the diagnostic utility of circulating S-adenosylmethionine is apparent. As a group, patients with *P. carinii* are readily identifiable by low circulating S-adenosylmethionine levels. Furthermore, the inventor has made the observation that successful treatment of *P. carinii* infection results in a chance in circulating S-adenosylmethionine levels towards the levels in non-*P. carinii* infected individuals, such that monitoring the change over time in S-adenosylmethionine levels may be used to track successful clinical response, as well as early identification of individuals unresponsive to treatment.

Circulating S-adenosylmethionine levels may be measured by any method capable of detecting the levels over the ranges described herein, i.e., from about 500 nM down to 0.5 nM and lower. Non-limiting methods that may be used include, for example reverse phase ion-pair chromatography as described in Merali et al., 2000, *J. Biol. Chem.* 275: 14958-14963). In this method, 80 µl serum or plasma was mixed with 20 µl of 10% perchloric acid. After centrifugation at 5000×g for 5 min to remove precipitated material, the supernatants were collected for HPLC assay. An internal standard, S-adenosyl ethionine (SAE), was added to all samples to a concentration of 13.9 µM. Chromatographic separation was achieved with an octyl silanol (C8) reverse phase column (3.9×150 mm, Rainin Instrument Co., Woburn, Mass.) using an isocratic mobile phase of 40 mM ammonium phosphate, 5 mM heptane sulfonic acid (ion pairing reagent), and 3.6% acetonitrile (pH 5.0). The injection volume was 70 µl and the flow rate was 1.0 ml min 1. Absorbance was detected by a photodiode array (Waters 996) and recorded at 1-nm intervals from 200 to 500 nm. Chromatograms were extracted at 257 nm. Absorbance data at wavelengths other than 257 nm were used for Millennium™ (Waters Corp., Milford, Mass.) software peak purity algorithms and for three-dimensional computer displays which were helpful for initial method development.

In another example, S-adenosylmethionine was extracted from plasma exactly as above. Pre-column derivitization was performed as described previously for polyamine analysis (Merali, S., and Clarkson, A. B., Jr. (1996) *J. Chromatogr. Sect. B Biomed. Appl.* 675, 321-326). An internal standard of 5 µl (5 µg ml-1 of 1,7-diaminoheptane) and 45 =l of borate buffer (0.2 M sodium borate, 1 mM EDTA, pH 8.8) was added to 30 µl of clarified plasma. After mixing, 20 µl of AccQ.Fluor reagent was added. HPLC conditions were as described previously for polyamine analysis (Merali et al., ibid.). This method was calibrated and validated by demonstrating linearity (r>0.99) and sensitivity in the subpicomole range using purchased authentic S-adenosylmethionine.

The foregoing are merely examples of methods for measuring S-adenosylmethionine in a sample and are in no way limiting to the practice of the invention. The procedures may be carried out using automated, semiautomated and manual methods, including a test strip format.

Thus, the method of the invention may be used for diagnosis of *P. carinii* infection. As is apparent from the data presented herein, individuals without *P. carinii* infection have a mean S-adenosylmethionine level in the plasma of about 105 nM, and *P.-carinii*-infected patients a level of about 2 nM. A cutoff value of two standard deviations below the mean uninfected patient, about 25 nM, may be used as a value below which a diagnosis of *P. carinii* may be made. Of course, these values may be further refined on study of a larger population of patients, and those with different underlying or co-morbid diseases or conditions, and a normal range and abnormal range for diagnosis of *P. carinii* infections, may be made. The present invention embraces such further fine-tuning of the normal (reference) and suspicion/diagnosis of *P. carinii* ranges.

Furthermore, the methods of the invention are also applicable to the monitoring of *P. carinii* infection over time, such as may be desirable in following the course of treatment to ensure that the chemotherapeutic or other agent or treatment means is effective. As will be shown in the examples below, the significantly reduced level of circulating S-adenosylmethionine attendant to *P. carinii* infection rises during effective treatment. Thus, periodically monitoring a patient's circulating S-adenosylmethionine level during treatment indicates the effectiveness of treatment, and may be used to alert the health care practitioner of a resistant or ineffective treatment, such that altering the dose or switching therapeutic agents can be done earlier than is now possible. The monitoring of course of therapy is not limited to any particular treatment regimen, type of agent, nor co-morbid condition of the patient, such as, in a preferred embodiment, the monitoring of an HIV-infected patient for resolution of a *P. carinii* infection.

The diagnostic methods of the invention may be used in conjunction with other diagnostic methods for *P. carinii* infection, including but not limited to clinical observation, bronchiolar lavage, PCR methods, etc. It may provide a sole diagnosis or serve as a confirmatory diagnosis based on another method. In one embodiment, S-adenosylmethionine levels are determined on any blood sample from a patient with any immunosuppressive condition, to serve as an early diagnosis for *P. carinii* before any overt clinical manifestations of disease appear. This provides an early opportunity to treat. For example. HIV-infected patients appear more susceptible to *P. carinii* infection when the CD4+ count is less than or equal to 200. The S-adenosylmethionine test may be performed on any HIV-infected patient at or below this CD4+ level, to provide ample and early opportunity to treat an infection.

As noted above, a preferred circulating bodily fluid is plasma or serum, preferably plasma, yet serum or whole blood may also be use for the determination of S-adenosylmethionine activity. Certain processing differences depending on the type of sample may be required, well within the purview of the skilled artisan.

As noted above, the applicability of the present methods is particularly suited to human patients susceptible to *P. carinii* infection, including but not limited to patients infected with HIV or with AIDS, immunosuppressed patients, cancer patients, and other conditions in which immune suppression is a condition of the disease or is a sequela of therapy. The immunosuppression induced by HIV infection is well known. Transplant patients and others receiving chronic immunosuppressive therapy for preventing rejection or chronic inflammatory conditions are also candidates. Cancer patients undergoing chemotherapy in which the immune system is vulnerable to suppression are also candidates. These are merely exemplary of the variety of susceptible patients that may, if infected with *P. carinii* or suspected of being infected with *P. carinii*, benefit from both the diagnosis of *P. carinii* infection and the monitoring of the effectiveness of therapy.

The following examples are presented in order to more fully illustrate the preferred embodiments of the invention. They should in no way be construed, however, as limiting the broad scope of the invention.

EXAMPLE 1

Plasma S-adenosylmethionine levels were determined using the HPLC method described hereinabove on a group of asymptomatic HIV-infected individuals as well as on groups of HIV-infected individuals with bacterial pneumonia, cryptococcosis, tuberculosis, and infection with *P. carinii* (pneumocystosis). Representative data on these groups is shown in the Table below, and the complete data, including means, ranges, and standard deviations are plotted in FIG. 1.

Plasma S-Adenosylmethionine of Individual Patients (nM)

| Plasma S-Adenosylmethionine of Individual Patients (nM0 | | | | | | | | | | | | | Mean |
|---|---|---|---|---|---|---|---|---|---|---|---|---|---|
| Controls | 114 | 87 | 120 | 99 | 114 | 90 | 128 | 116 | 108 | 86 | 105 | 108 | 106 |
| PCP | 0.99 | 0.50 | 0.50 | 15.0 | 0.50 | 0.50 | 0.50 | 0.50 | 0.50 | 0.50 | 0.50 | 0.50 | 2 |
| Fungal Infections | 128 | 167 | 216 | | | | | | | | | | 170 |
| Bacterial Infections | 189 | 76 | 239 | 122 | 106 | 106 | 170 | 168 | | | | | 147 |
| HIV off Antiretro viral therapy | 112 | 57 | 87 | 98 | | | | | | | | | 89 |
| HIV on Antiretro viral therapy | 99 | 100 | 79 | 68 | 72 | 130 | 127 | | | | | | 96 |

As can be seen from the table, the majority of patients with pneumocystosis have very low levels of S-adenosylmethionine, at the level of detectability (0.5 nM) of the assay. In contract, asymptomatic, control individuals as well as those with other infections have normal or values elevated above normal.

These and other data are plotted in FIG. 1. The data presented includes HIV+ patients with PCP (n=15), bacterial pneumonia (n=18), cryptococcosis (n=5), tuberculosis (n=2), other illnesses (3), or HIV+ patients without other diagnosis (6). Plasma S-adenosylmethionine levels were measured by HPLC on admission or at a clinic visit. As shown in the table or figure, S-adenosylmethionine levels were reduced dramatically in those with PCP and were below the limit of detection (0.5 nM) in 14/15 cases (in nM: median <0.5, range <0.5-8 for PCP, versus 106, range 44-216 for all others, P<0.001, Wilcoxon Test). The area under the ROC curve was 99%.

Figure 2:
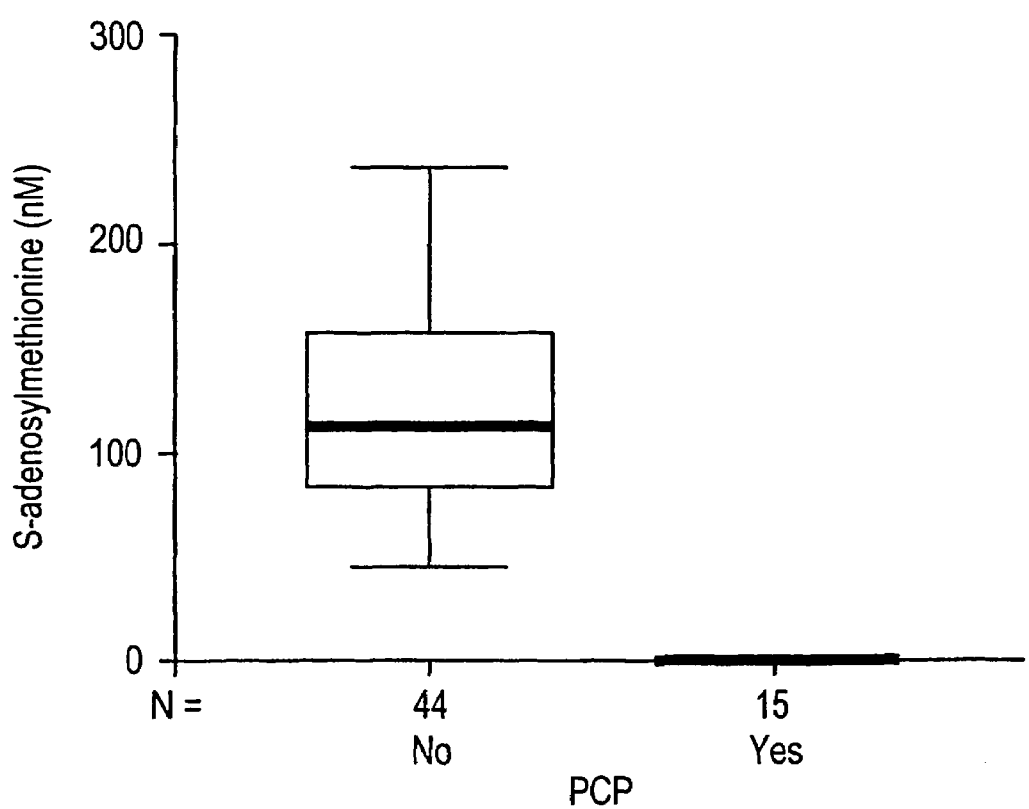
FIG. 2 compares plasma S-adenosylmethionine levels in the pneumocystosis patients versus all other patients in the study.

FIG. 2 compares the level of S-adenosylmethionine in HIV-infected, pneumocystosis patients with all of the other patients in the study. The figure shows the mean, range, and standard deviation of the values.

EXAMPLE 2

Individuals with *P. carinii* infections may be monitored over time to track the effectiveness of therapy. FIG. 3 shows S-adenosylmethionine data from 15 patients with PCP (8 confirmed, 7 diagnosed clinically) and compares them with 18 patients with bacterial pneumonia (BP). Plasma S-adenosylmethionine levels were measured by HPLC on admission, and at various points during the course of treatment. S-Adenosylmethionine levels were depressed in all patients with PCP (below the limit of detection 0.5 nM in 14/15) and rose during the first week of treatment but remained below the 95% tolerance limit for a group healthy laboratory controls (80-140 nM). Levels of S-adenosylmethionine in those with bacterial pneumonia (BP) were not depressed and did not change systematically during the treatment period. Two of the PCP patients died during the study: one on day 3 of treatment with persistently low S-adenosylmethionine levels, and another (with concomitant aspergillosis) on day 5 with rising levels.

Thus, persisting suppression of S-adenosylmethionine levels during treatment may reflect treatment failure, and indicates the utility of the monitoring of S-adenosylmethionine levels for early detection of resistance to treatment.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference herein in their entireties.

What is claimed is:

1. A method for identifying the presence of a *Pneumocystis carinii* infection in a human comprising the steps of
   a) obtaining a blood sample from said human;
   b) measuring the level of S-adenosylmethionine in said blood sample; and
   c) determining whether the level of S-adenosylmethionine in said sample is below about 25 nM;

wherein a level of S-adenosylmethionine below about 25 nM is indicative of a *Pneumocystis carinii* infection.

2. The method of claim 1 wherein said human is infected with HIV, has AIDS, has cancer, is immunosuppressed, or is otherwise susceptible to infection by *Pneumocystis carinii*.

3. The method of claim 1, wherein said blood sample is plasma.

* * * * *